United States Patent [19]
Wiedner

[11] Patent Number: 4,649,577
[45] Date of Patent: Mar. 17, 1987

[54] PROTECTIVE GOGGLES

[75] Inventor: Klaus Wiedner, Fürth, Fed. Rep. of Germany

[73] Assignee: Uvex Winter Optik GmbH, Fürth, Fed. Rep. of Germany

[21] Appl. No.: 821,007
[22] Filed: Jan. 22, 1986
[51] Int. Cl.$^4$ .................................................. A61F 9/02
[52] U.S. Cl. ................................................ 2/436; 2/437
[58] Field of Search ............................ 2/436, 437, 452

[56] References Cited

U.S. PATENT DOCUMENTS

| | | | |
|---|---|---|---|
| 1,670,638 | 5/1928 | Shindel | 2/437 |
| 1,779,155 | 10/1930 | Baker | 2/437 |
| 1,838,649 | 12/1931 | Baker | 2/437 |
| 2,085,844 | 7/1937 | Baker | 2/437 |
| 2,410,184 | 10/1946 | Schauweker | 2/437 |
| 3,141,172 | 7/1964 | Hirschmann | 2/436 |
| 3,418,658 | 12/1968 | Danico | 2/436 |
| 4,027,342 | 6/1977 | Hirschmann | 2/436 |

Primary Examiner—Louis K. Rimrodt
Attorney, Agent, or Firm—Browdy and Neimark

[57] ABSTRACT

The invention is directed to protective goggles having a lens through which the wearer sees and a frame, receiving the lens, of elastically deformable material and having securing devices for a fastening strap disposed on the outsides of the frame. To attain advantageous ventilation of the interior of the goggles and to enable manufacture and assembly at a favorable cost, the securing devices can be joined in a form-fitting manner to the frame and have vent openings for ventilating the interior of the goggles. In particular, the securing devices can be snapped into recesses in the frame, and vent openings formed in the securing devices can be selectively opened or closed by means of a covering plate that is attached by screwing.

2 Claims, 3 Drawing Figures

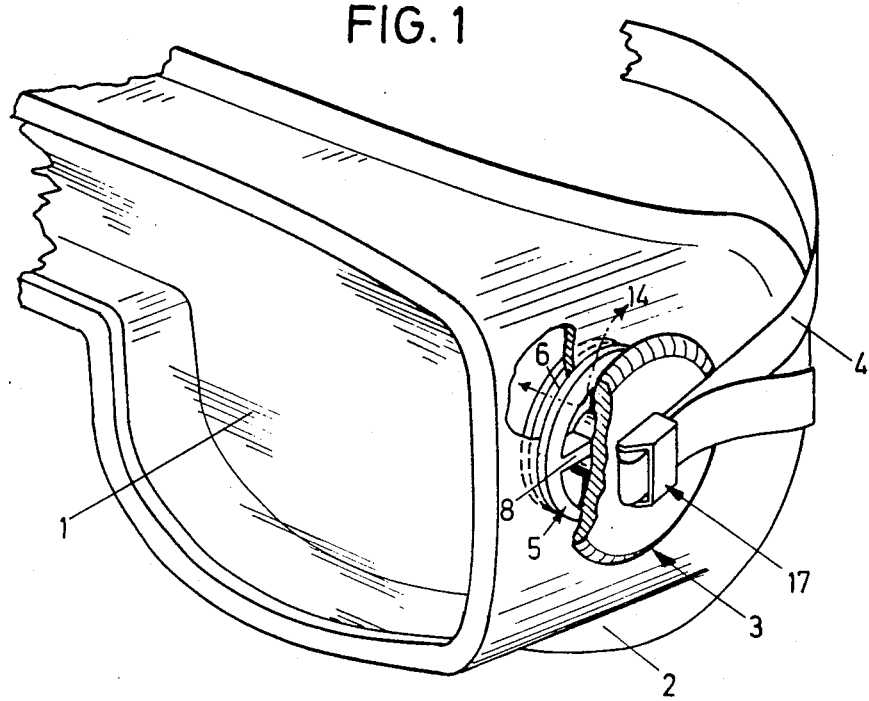
FIG. 1
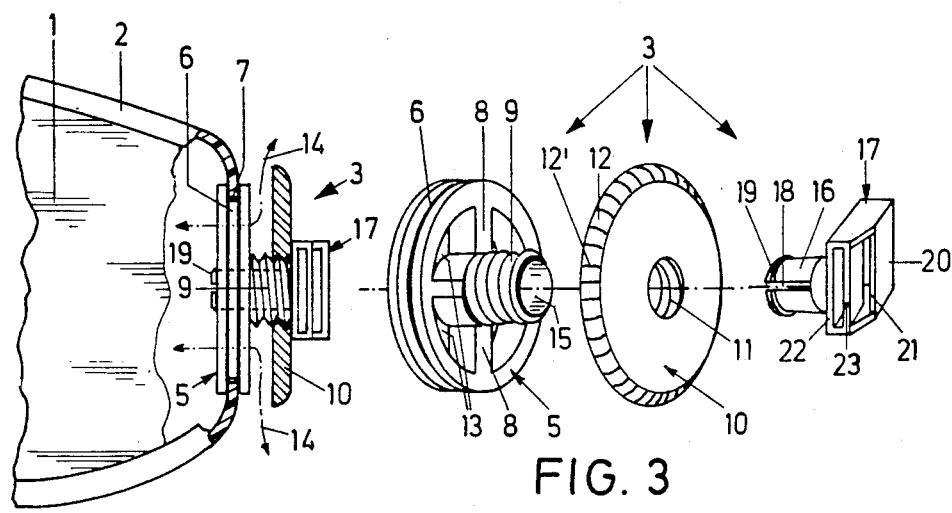
FIG. 2
FIG. 3

PROTECTIVE GOGGLES

FIELD OF THE INVENTION

The present invention is directed to protective goggles which have a clear panel or lens through which the wearer can see and a frame, receiving the panel or lens, of elastically deformable material. Securing devices for a fastening strap are disposed on the outside of the frame.

BACKGROUND OF THE INVENTION

Protective goggles of this type, which are typically known as full-view goggles, are used for example as safety goggles in the workplace, or as ski goggles. In such goggles, it is known to provide vent openings in the frame itself, to prevent fogging of the lens as much as possible. The fastening straps provided for fastening such protective goggles are attached to securing devices, which either are spray-molded onto the frame or must be mounted thereon, the latter being relatively labor-intensive.

SUMMARY OF THE INVENTION

It is accordingly the object of the present invention to embody protective goggles of the above type such that, while they can be simply fabricated by injection molding and while the securing devices of the fastening strap can be mounted relatively inexpensively, good ventilation of the interior of the goggles is simultaneously assured.

This object is attained in accordance with the invention by providing that the securing devices can be joined to the frame in a form-fitting manner and include vent openings for the interior of the goggles. As a result, the injection mold for the frame can be produced at a favorable cost; the securing devices can be mounted quickly and easily; and a defined ventilation is possible through vent openings integrated with the securing devices.

It is advantageously provided that the securing devices have an encircling groove and can be snapped into a corresponding recess in the frame in such a manner that the edge of the recess comes to rest in the groove. By utilizing the inherent elasticity of the frame, a securing means is thereby attained which enables mounting without requiring any additional tools of any kind.

It can also be provided that the securing devices have a base plate, the vent openings being embodied as perforations in this base plate and the base plate having a central threaded portion, onto which a covering plate for the vent openings can be threaded. Because of the correspondingly provided, screw-mounted covering plate, the vent openings can be closed if this provision is considered desirable, or the degree to which they are opened can be adjusted by rotating the covering plate accordingly. At the same time, drafts can be prevented from entering directly into the interior of the goggles.

It is advantageously provided that the covering plate is in the form of a circular disk, having a ribbed rim area. This enables particularly easy manipulation of the covering plate in order to open or close the vent openings.

A further favorable embodiment is distinguished by the provision of a central bore for the threaded portion and the base plate, into which bore a protruding extension of a swivelling device for the fastening strap can be inserted. Preferably the protruding extension can be locked into a detent in the central bore.

As a result of this embodiment, mounting the swivelling device and thus mounting of the entire apparatus is made extraordinarily much more simple. At the same time, the plate-like inside of the swivelling device represents a stop for the covering plate when the covering plate is in its fully open position.

Further features, advantages and details of the invention will become apparent from the ensuing description of a preferred embodiment, taken in conjunction with the drawings.

BRIEF DESCRIPTION OF THE DRAWINGS

FIG. 1 is a fragmentary perspective view of a pair of protective goggles according to the invention, which has been partially cut away in the area of the securing device;

FIG. 2 is a fragmentary section taken through the area where a securing device is attached; and FIG. 3 is an exploded view of the parts of a securing device.

DESCRIPTION OF THE PREFERRED EMBODIMENT

A pair of protective goggles shown in the drawing, such as safety goggles for use in the workplace, includes a panel or lens 1 through which the wearer can see and a frame 2 of elastically deformable plastic. A fastening strap 4 is fixed to the frame 2 by means of securing devices 3, only one of which is shown in the drawing.

Each securing device 3 includes a base plate 5. The circular base plate 5, like all the other parts of each securing device 3, is injection molded from plastic. It has an encircling groove 6. With the aid of this groove, the base plate 5 and thus the securing device 3 can be inserted in a form-fitting manner, that is, snapped, into a corresponding circular-disk-shaped recess 7 of the frame 2, as shown particularly in FIG. 2.

The base plate 5 also has spokes 8, four in number in the exemplary embodiment, which support a threaded extension 9 that extends outward when in the inserted state. A covering plate 10 which has a threaded bore 11 can be screwed onto this threaded extension 9. The covering plate 10 is basically in the shape of a circular disk, the diameter of which is somewhat larger than that of the base plate 5. The outer rim 12 of the covering plate 10 is provided with ribbing 12′, which facilitates rotating the covering plate 10.

Free openings are formed in the base plate 5 between the spokes 8 and serve as vent openings 13. If the covering plate 10 is screwed all the way onto the threaded extension 9, these vent openings 13 can be fully covered by the covering plate 10; on the other hand, if the covering plate 10 is screwed in the opposite direction, the vent openings 13 can be opened to a variable extent. As the arrows 14 in FIG. 2 show, drafts cannot penetrate directly through the vent openings 13 and so the wearer of the goggles will not feel a draft.

The threaded extension 9, and hence the base plate 5, has a central bore 15. A protrusion 16 of a swivelling device 17 for the fastening strap 4 can be inserted into this bore 15. The protrusion 16 has longitudinal slits 18 and on its free front end is provided with an encircling detent bead 19. The swivelling device per se is embodied by a box-like body 20 having two parallel outer walls 21, 22 and a crossbar 23, about which the fastening strap 4 is looped, as shown in FIG. 1.

The swivelling device is secured to the base plate 5 by inserting the protrusion 16 into the bore 16, thereby compressing the protrusion 16 by means of the slits 18. Once the detent bead 19, after insertion, has reemerged from the other end of the bore 15, it is pressed outward, because of the inherent elasticity of the plastic material of which the protrusion 16 is made, and grips the inner rim of the bore 15, as shown in FIG. 2, thereby axially fixing the swivelling device. At the same time, the outer wall 22 of the swivelling device 17 then forms a stop for the covering plate 10, as shown particularly in FIG. 2, whenever the covering plate 10 is unscrewed all the way to the outside and uncovers the vent openings 13.

What is claimed is:

1. Protective goggles having a lens and a frame for receiving the lens, the frame made of elastically deformable material, having securing devices for a fastening strap disposed on the outside of the frame;

wherein the securing devices can be joined in a form-fitting manner to the frame and have vent openings for ventilating the interior of the goggles;

wherein the securing devices have an encircling groove and can be snapped into a corresponding recess of the frame in such a manner that the rim of the recess comes to rest in the groove;

the securing devices have a base plate, the vent openings are perforations of a base plate, and the base plate has a central threaded portion onto which a covering plate for the vent openings can be screwed;

wherein the covering plate is in the form of a circular disk and has a ribbed rim area, whereby by simple manipulation the size of the vent openings can easily and conveniently be changed.

2. The protective goggles of claim 1 wherein the threaded portion and the base plate have a central bore into which a protrusion of a swivelling device for the fastening strap can be inserted.

* * * * *